(12) United States Patent
Olmstead et al.

(10) Patent No.: US 12,370,145 B2
(45) Date of Patent: Jul. 29, 2025

(54) THERAPEUTIC AGENT NANOPARTICLES AND METHODS OF PREPARATION

(71) Applicant: Nano PharmaSolutions, Inc., San Diego, CA (US)

(72) Inventors: Kay Olmstead, Escondido, CA (US); Saeyeon Lee, Seongnam (KR); Seok-Keun Koh, Seoul (KR)

(73) Assignee: Nano PharmaSolutions, Inc., San Diego, CA (US)

( * ) Notice: Subject to any disclaimer, the term of this patent is extended or adjusted under 35 U.S.C. 154(b) by 410 days.

(21) Appl. No.: 17/178,456

(22) Filed: Feb. 18, 2021

(65) Prior Publication Data

US 2021/0290543 A1 Sep. 23, 2021

Related U.S. Application Data

(60) Provisional application No. 62/978,773, filed on Feb. 19, 2020.

(51) Int. Cl.
*A61K 9/16* (2006.01)
*A61K 9/14* (2006.01)
(Continued)

(52) U.S. Cl.
CPC ............. *A61K 9/1676* (2013.01); *A61K 9/14* (2013.01); *A61K 9/1623* (2013.01); *A61K 9/1635* (2013.01); *A61K 9/1652* (2013.01); *A61K 9/1694* (2013.01); *A61K 31/05* (2013.01); *A61K 31/122* (2013.01); *A61K 31/192* (2013.01); *A61K 31/381* (2013.01);
(Continued)

(58) Field of Classification Search
None
See application file for complete search history.

(56) References Cited

U.S. PATENT DOCUMENTS 6,316,029 B1 * 11/2001 Jain ...................... A61K 9/1617
424/501
8,216,495 B2 * 7/2012 Janssens .............. A61K 9/1641
264/5
(Continued)

FOREIGN PATENT DOCUMENTS

CN 107912023 A 10/2020
EP 1131054 B1 9/2001
(Continued)

OTHER PUBLICATIONS

Meruva et al.Formulation and performance of Irbesrtan microcrystalline suspension and granulatedor bead-layered dried powders—Part I, Internation Journal of Pharmaceutics 568, 118189, pp. 1-10 (Year: 2019).*

(Continued)

*Primary Examiner* — Lakshmi S Channavajjala
(74) *Attorney, Agent, or Firm* — Lin Yu, Esq.; Juniv LLP

(57) ABSTRACT

Provided herein is a coated particle comprising: (i) a microparticle that comprises a pharmaceutically acceptable excipient and (ii) nanoparticles of a therapeutic agent, wherein the surface of the microparticle is coated with the nanoparticles. Also provided herein is a pharmaceutical composition comprising the coated particle. Furthermore, provided herein are methods of their preparation.

19 Claims, 1 Drawing Sheet

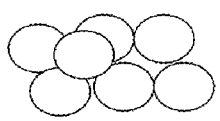 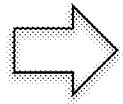 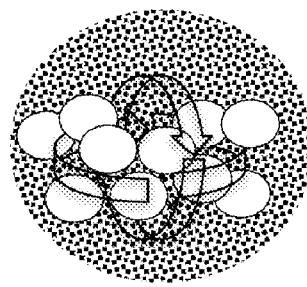 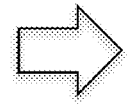 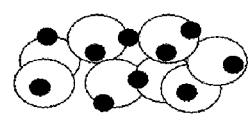

Microparticles → Contacting with a Vapor of a Therapeutic agent → Coated Particles

(51) Int. Cl.
| | |
|---|---|
| A61K 9/50 | (2006.01) |
| A61K 31/05 | (2006.01) |
| A61K 31/122 | (2006.01) |
| A61K 31/192 | (2006.01) |
| A61K 31/381 | (2006.01) |
| A61K 31/4422 | (2006.01) |
| A61K 31/5415 | (2006.01) |
| A61K 31/55 | (2006.01) |
| A61K 47/26 | (2006.01) |

(52) U.S. Cl.
CPC ...... *A61K 31/4422* (2013.01); *A61K 31/5415* (2013.01); *A61K 31/55* (2013.01)

(56) References Cited

U.S. PATENT DOCUMENTS

| | | | |
|---|---|---|---|
| 9,801,820 | B2 | 10/2017 | To et al. |
| 10,286,075 | B2 | 5/2019 | Townley et al. |
| 2008/0057129 | A1* | 3/2008 | Lerner .................... A61P 31/04 514/738 |
| 2018/0214551 | A1 | 8/2018 | Townley et al. |
| 2018/0312951 | A1 | 11/2018 | Martin et al. |

FOREIGN PATENT DOCUMENTS

| | | | | |
|---|---|---|---|---|
| EP | 2050437 | A1 | 4/2009 | |
| JP | 2016503411 | A | 2/2016 | |
| KR | 100644219 | B1 | 11/2006 | |
| WO | 2008045022 | A2 | 4/2008 | |
| WO | 2012147901 | A1 | 11/2012 | |
| WO | WO-2014027334 | A2 * | 2/2014 | ........... A61K 31/549 |
| WO | 2014074808 | A1 | 5/2014 | |

OTHER PUBLICATIONS

Bhakay et al . Recovery of BCS Class II drugs during aqueous redispersion of core-shell type nanocomposite particles produced via fluidized bed coating. Powder Technology, 236:221-234 (Year: 2013).*

Beck et al., "Dexamethasone-loaded nanoparticle-coated microparticles: correlation between in vitro drug release and drug transport across Caco-2 cell monolayers," Eur. J. Pharm. Biopharm. 2007, 67, 18-30.

Da Fonseca et al., "Nanocapsule@xerogel microparticles containing sodium diclofenac: a new strategy to control the release of drugs," Int. J. Pharm. 2008, 358, 292-5.

Guterres et al., "Spray-drying technique to prepare innovative nanoparticulated formulations for drug administration: a brief overview," Braz. J. Phys. 2009, 39, 205-9.

Duret et al., "New inhalation-optimized itraconazole nanoparticle-based dry powders for the treatment of invasive pulmonary aspergillosis," Int. J. Nanomedicine 2012, 7, 5475-89.

Baldo et al, "Organic vapor phase deposition," Adv. Mater. 1999, 10, 1505-1514.

Challa et al., "Cyclodextrins in drug delivery: an updated review," AAPS PharmSciTech 2005, 6, E329-E357.

Kollipara and Gandhi, "Pharmacokinetic aspects and in vitro-in vivo correlation potential for lipid-based formulations," Acta Pharm. Sin. B 2014, 4, 333-349.

Salama, "Spray drying as an advantageous strategy for enhancing pharmaceuticals bioavailability," Drug Deliv. Transl. Res. 2020, 10, 1-12.

Savjani et al., "Drug solubility: importance and enhancement techniques," ISRN Pharm. 2012, 2012, 195727.

Raula et al., "A novel gas phase method for the combined synthesis and coating of pharmaceutical particles," Pharm. Res. 2008, 25, 242-5.

Raula et al., "Gas-phase synthesis of l-leucine-coated micrometer-sized salbutamol sulphate and sodium chloride particles," Powder Technol. 2008, 187, 289-97.

* cited by examiner

Microparticles → Contacting with a Vapor of a Therapeutic agent → Coated Particles

THERAPEUTIC AGENT NANOPARTICLES AND METHODS OF PREPARATION

CROSS REFERENCE TO RELATED APPLICATION

This application claims the benefit of U.S. Provisional Application No. 62/978,773, filed Feb. 19, 2020; the disclosure of which is incorporated herein by reference in its entirety.

FIELD

Provided herein is a coated particle comprising: (i) a microparticle that comprises a pharmaceutically acceptable excipient and (ii) nanoparticles of a therapeutic agent, wherein the surface of the microparticle is coated with the nanoparticles. Also provided herein is a pharmaceutical composition comprising the coated particle. Furthermore, provided herein are methods of their preparation.

BACKGROUND

Poor water solubility presents a major challenge in drug formulation. Savjani et al., *ISRN Pharm.* 2012, 2012, 195727. More than 70% of small-molecule new chemical entities (NCE) and about 40% of the currently marketed drugs have poor water solubility. Kollipara and Gandhi, *Acta Pharm. Sin. B* 2014, 4, 333-349. Various techniques have been developed to enhance the solubility of poorly soluble drugs, including particle size reduction, crystal engineering, salt formation, solid dispersion, use of surfactant, and complexation. See, e.g., Id.; Challa et al., *AAPS PharmSciTech* 2005, 6, E329-E357; Salama, *Drug Deliv. Transl. Res.* 2020, 10, 1-12. Despite advances in formulation technology, poor water solubility still remains a major hurdle in small-molecule drug development. Therefore, there is a need for an effective and robust technology to formulate poorly soluble small molecules for therapeutic applications.

SUMMARY OF THE DISCLOSURE

Provided herein is a coated particle comprising: (i) a microparticle that comprises a pharmaceutically acceptable excipient and (ii) nanoparticles, each comprising a therapeutic agent; wherein the microparticle is surface-coated with the nanoparticles.

Also provided herein is a pharmaceutical composition comprising coated particles, each particle comprising: (i) a microparticle that comprises a pharmaceutically acceptable excipient and (ii) nanoparticles of a therapeutic agent, wherein the microparticle is surface-coated with the nanoparticles.

Additionally, provided herein is a method of preparing coated particles, each particle comprising: (i) a microparticle that comprises a pharmaceutically acceptable excipient and (ii) nanoparticles of a therapeutic agent, comprising the steps of:
  a. vaporizing the therapeutic agent at a first predetermined temperature under a predetermined vacuum pressure to form a vapor; and
  b. depositing the vapor on the surfaces of the microparticles at a predetermined agitation speed and a second predetermined temperature under the predetermined vacuum pressure to form the nanoparticles on the surfaces of the microparticles, thus forming the coated particles.

Furthermore, provided herein is a method of preparing nanoparticles of a therapeutic agent, comprising the steps of:
  a. vaporizing the therapeutic agent at a first predetermined temperature under a predetermined vacuum pressure to form a vapor; and
  b. depositing the vapor on the surface of a microparticle comprising a pharmaceutically acceptable excipient at a predetermined agitation speed and a second predetermined temperature under the predetermined vacuum pressure to form the nanoparticles on the surface of the microparticle.

Provided herein are coated particles, each particle comprising: (i) a microparticle that comprises a pharmaceutically acceptable excipient and (ii) nanoparticles of a therapeutic agent; wherein the coated particles are prepared by a method comprising the steps of:
  a. vaporizing the therapeutic agent at a first predetermined temperature under a predetermined vacuum pressure to form a vapor; and
  b. depositing the vapor on the surfaces of the microparticles at a predetermined agitation speed and a second predetermined temperature under the predetermined vacuum pressure to form the nanoparticles on the surfaces of the microparticles, thus forming the coated particles.

Provided herein are nanoparticles of a therapeutic agent, which are prepared by a method comprising the steps of:
  a. vaporizing the therapeutic agent at a first predetermined temperature under a predetermined vacuum pressure to form a vapor; and
  b. depositing the vapor on the surface of a microparticle comprising a pharmaceutically acceptable excipient at a predetermined agitation speed and a second predetermined temperature under the predetermined vacuum pressure to form the nanoparticles on the surface of the microparticle.

Provided herein is a pharmaceutical composition comprising coated particles, each particle comprising: (i) a microparticle that comprises a pharmaceutically acceptable excipient and (ii) nanoparticles of a therapeutic agent; wherein the coated particles are prepared by a method comprising the steps of:
  a. vaporizing the therapeutic agent at a first predetermined temperature under a predetermined vacuum pressure to form a vapor; and
  b. depositing the vapor on the surfaces of the microparticles at a predetermined agitation speed and a second predetermined temperature under the predetermined vacuum pressure to form the nanoparticles on the surfaces of the microparticles, thus forming the coated particles.

Provided herein is a pharmaceutical composition comprising nanoparticles of a therapeutic agent, which are prepared by a method comprising the steps of:
  a. vaporizing the therapeutic agent at a first predetermined temperature under a predetermined vacuum pressure to form a vapor; and
  b. depositing the vapor on the surface of a microparticle comprising a pharmaceutically acceptable excipient at a predetermined agitation speed and a second predetermined temperature under the predetermined vacuum pressure to form the nanoparticles on the surface of the microparticle.

Provided herein is a batch of coated particles, each particle comprising: (i) a microparticle that comprises a pharmaceutically acceptable excipient and (ii) nanoparticles of a therapeutic agent; wherein the coated particles are prepared by a method comprising the steps of:
a. vaporizing the therapeutic agent at a first predetermined temperature under a predetermined vacuum pressure to form a vapor; and
b. depositing the vapor on the surfaces of the microparticles at a predetermined agitation speed and a second predetermined temperature under the predetermined vacuum pressure to form the nanoparticles on the surfaces of the microparticles, thus forming the coated particles.

Provided herein is a batch of nanoparticles of a therapeutic agent, which are prepared by a method comprising the steps of:
a. vaporizing the therapeutic agent at a first predetermined temperature under a predetermined vacuum pressure to form a vapor; and
b. depositing the vapor on the surface of a microparticle comprising a pharmaceutically acceptable excipient at a predetermined agitation speed and a second predetermined temperature under the predetermined vacuum pressure to form the nanoparticles on the surface of the microparticle.

Provided herein is a batch of a pharmaceutical composition comprising coated particles, each particle comprising: (i) a microparticle that comprises a pharmaceutically acceptable excipient and (ii) nanoparticles of a therapeutic agent; wherein the coated particles are prepared by a method comprising the steps of:
a. vaporizing the therapeutic agent at a first predetermined temperature under a predetermined vacuum pressure to form a vapor; and
b. depositing the vapor on the surfaces of the microparticles at a predetermined agitation speed and a second predetermined temperature under the predetermined vacuum pressure to form the nanoparticles on the surfaces of the microparticles, thus forming the coated particles.

Provided herein is a batch of a pharmaceutical composition comprising nanoparticles of a therapeutic agent and a pharmaceutical acceptable excipient, wherein the nanoparticles are prepared by a method comprising the steps of:
a. vaporizing the therapeutic agent at a predetermined temperature under a first predetermined vacuum pressure to form a vapor; and
b. depositing the vapor on the surface of a microparticle comprising the pharmaceutically acceptable excipient at a predetermined agitation speed and a second predetermined temperature under the predetermined vacuum pressure to form the nanoparticles on the surface of the microparticle.

BRIEF DESCRIPTION OF THE DRAWINGS

FIG. 1 illustrates the formation of nanoparticles of a therapeutic agent on the surfaces of microparticles of a hydrophilic excipient by contacting the microparticles with a vapor of the therapeutic agent.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, and commensurate with a reasonable benefit/risk ratio. See, e.g., *Remington: The Science and Practice of Pharmacy*, 22nd ed.; Allen Ed.; Pharmaceutical Press: London, 2012; *Handbook of Pharmaceutical Excipients*, 8th ed.; Sheskey et al., Eds.; Pharmaceutical Press: London, 2017; *Handbook of Pharmaceutical Additives*, 3rd ed.; Ash and Ash Eds.; Synapse Information Resources: 2007; *Pharmaceutical Preformulation and Formulation*, 2nd ed.; Gibson Ed.; Drugs and the Pharmaceutical Sciences 199; Informa Healthcare: New York, NY, 2009.

The term "about" or "approximately" means an acceptable error for a particular value as determined by one of ordinary skill in the art, which depends in part on how the value is measured or determined. In certain embodiments, the term "about" or "approximately" means within 1, 2, or 3 standard deviations. In certain embodiments, the term "about" or "approximately" means within 25%, 20%, 15%, 10%, 9%, 8%, 7%, 6%, 5%, 4%, 3%, 2%, 1%, 0.5%, or 0.05% of a given value or range.

The term "batch" refers to a defined quantity of a compound, material, or drug product processed in a process or series of processes so that it is homogeneous within specified limits. To complete certain stages of manufacture, it may be necessary to divide a batch into a number of sub-batches, which are later brought together to form a final homogeneous batch. In the case of continuous manufacture, the batch corresponds to a defined fraction of the production, characterized by its intended homogeneity. In manufacturing a drug product, synthetic intermediates and the drug product are each identified by a batch number.

Coated Particles and Nanoparticles

In one embodiment, provided herein is a coated particle comprising: (i) a microparticle that comprises a pharmaceutically acceptable excipient and (ii) nanoparticles, each comprising a therapeutic agent; wherein the surface of the microparticle is coated with the nanoparticles.

In certain embodiments, the surface of the microparticle is coated with a layer of the nanoparticles. In certain embodiments, the surface of the microparticle is substantially coated with a layer of the nanoparticles. In certain embodiments, the surface of the microparticle is coated with a thin layer of the nanoparticles. In certain embodiments, the surface of the microparticle is substantially coated with a thin layer of the nanoparticles. In certain embodiments, the surface of the microparticle is coated with a single layer of the nanoparticles. In certain embodiments, the surface of the microparticle is substantially coated with a single layer of the nanoparticles.

In certain embodiments, the pharmaceutically acceptable excipient in the coated particle provided herein is hydrophilic. In certain embodiments, the pharmaceutically acceptable excipient in the coated particle provided herein is water-soluble.

In certain embodiments, the pharmaceutically acceptable excipient in the coated particle provided herein is a sugar. In certain embodiments, the pharmaceutically acceptable excipient in the coated particle provided herein is dextrose, fructose, glucose, lactose, maltose, molasses, sucrose, trehalose, or a mixture thereof. In certain embodiments, the pharmaceutically acceptable excipient in the coated particle provided herein is dextrose, glucose, lactose, sucralose, sucrose, or a mixture thereof. In certain embodiments, the pharmaceutically acceptable excipient in the coated particle provided herein is dextrose. In certain embodiments, the pharmaceutically acceptable excipient in the coated particle provided herein is D-dextrose. In certain embodiments, the pharmaceutically acceptable excipient in the coated particle provided herein is fructose. In certain embodiments, the pharmaceutically acceptable excipient in the coated particle provided herein is glucose. In certain embodiments, the pharmaceutically acceptable excipient in the coated particle provided herein is lactose. In certain embodiments, the pharmaceutically acceptable excipient in the coated particle provided herein is maltose. In certain embodiments, the pharmaceutically acceptable excipient in the coated particle provided herein is molasses. In certain embodiments, the pharmaceutically acceptable excipient in the coated particle provided herein is sucrose. In certain embodiments, the pharmaceutically acceptable excipient in the coated particle provided herein is trehalose.

In certain embodiments, the pharmaceutically acceptable excipient in the coated particle provided herein is a sugar alcohol. In certain embodiments, the pharmaceutically acceptable excipient in the coated particle provided herein is arabitol, erythritol, fucitol, galactitol, iditol, inositol, isomalt, lactitol, maltitol, maltotritol, mannitol, ribitol, sorbitol, threitol, volemitol, xylitol, or a mixture thereof. In certain embodiments, the pharmaceutically acceptable excipient in the coated particle provided herein is erythritol, lactitol, maltitol, mannitol, sorbitol, xylitol, or a mixture thereof. In certain embodiments, the pharmaceutically acceptable excipient in the coated particle provided herein is arabitol. In certain embodiments, the pharmaceutically acceptable excipient in the coated particle provided herein is erythritol. In certain embodiments, the pharmaceutically acceptable excipient in the coated particle provided herein is fucitol. In certain embodiments, the pharmaceutically acceptable excipient in the coated particle provided herein is galactitol. In certain embodiments, the pharmaceutically acceptable excipient in the coated particle provided herein is iditol. In certain embodiments, the pharmaceutically acceptable excipient in the coated particle provided herein is inositol. In certain embodiments, the pharmaceutically acceptable excipient in the coated particle provided herein is isomalt. In certain embodiments, the pharmaceutically acceptable excipient in the coated particle provided herein is lactitol. In certain embodiments, the pharmaceutically acceptable excipient in the coated particle provided herein is maltitol. In certain embodiments, the pharmaceutically acceptable excipient in the coated particle provided herein is maltotritol. In certain embodiments, the pharmaceutically acceptable excipient in the coated particle provided herein is mannitol. In certain embodiments, the pharmaceutically acceptable excipient in the coated particle provided herein is ribitol. In certain embodiments, the pharmaceutically acceptable excipient in the coated particle provided herein is sorbitol. In certain embodiments, the pharmaceutically acceptable excipient in the coated particle provided herein is threitol. In certain embodiments, the pharmaceutically acceptable excipient in the coated particle provided herein is volemitol. In certain embodiments, the pharmaceutically acceptable excipient in the coated particle provided herein is xylitol.

In certain embodiments, the pharmaceutically acceptable excipient in the coated particle provided herein is glucose, hydroxypropyl cellulose (HPC), hydroxypropyl methylcellulose (HPMC), lactose, mannitol, or polyvinylpyrrolidone (PVP). In certain embodiments, the pharmaceutically acceptable excipient in the coated particle provided herein is glucose or mannitol. In certain embodiments, the pharmaceutically acceptable excipient in the coated particle provided herein is glucose. In certain embodiments, the pharmaceutically acceptable excipient in the coated particle provided herein HPC. In certain embodiments, the pharmaceutically acceptable excipient in the coated particle provided herein HPMC. In certain embodiments, the pharmaceutically acceptable excipient in the coated particle provided herein lactose. In certain embodiments, the pharmaceutically acceptable excipient in the coated particle provided herein mannitol. In certain embodiments, the pharmaceutically acceptable excipient in the coated particle provided herein PVP.

In certain embodiments, the microparticle in the coated particle provided herein has various shapes, including, but not limited to, a sphere, spheroid, platelet, fibril, or fiber. In certain embodiments, the microparticle in the coated particle provided herein is substantially spherical. In certain embodiments, the microparticle in the coated particle provided herein is spherical. In certain embodiments, the microparticle in the coated particle provided herein is spheroidal.

In certain embodiments, the microparticle in the coated particle provided herein has an average particle size (D50) ranging from about 1 to about 1,000 μm, from about 10 to about 500 μm, from about 20 to about 500 μm, from about 50 to about 300 μm, or from about 100 to about 300 μm. In certain embodiments, the microparticle in the coated particle provided herein has an average particle size ranging from about 1 to about 1,000 μm. In certain embodiments, the microparticle in the coated particle provided herein has an average particle size ranging from about 10 to about 500 μm. In certain embodiments, the microparticle in the coated particle provided herein has an average particle size ranging from about 20 to about 500 μm. In certain embodiments, the microparticle in the coated particle provided herein has an average particle size ranging from about 50 to about 300 μm. In certain embodiments, the microparticle in the coated particle provided herein has an average particle size ranging from about 100 to about 300 μm. In certain embodiments, the microparticle in the coated particle provided herein has an average particle size of about 50, about 100, about 150, about 200, about 250, about 300, about 350, about 400, about 450, or about 500 μm.

In certain embodiments, the microparticle in the coated particle provided herein has an average particle size ranging from about 1 to about 100 μm, from about 1 to about 50 μm, or from about 1 to about 25 μm. In certain embodiments, the microparticle in the coated particle provided herein has an average particle size ranging from about 1 to about 100 μm. In certain embodiments, the microparticle in the coated particle provided herein has an average particle size ranging from about 1 to about 50 μm. In certain embodiments, the microparticle in the coated particle provided herein has an average particle size ranging from about 1 to about 25 μm. In certain embodiments, the microparticle in the coated particle provided herein has an average particle size of about 5, about 10, about 15, about 20, about 25, about 30, about 35, about 40, about 45, or about 50 μm.

In another embodiment, provided herein is a coated particle comprising: (i) a microparticle that comprises mannitol and (ii) nanoparticles, each comprising a therapeutic agent; wherein the surface of the mannitol microparticle is coated with the nanoparticles.

In certain embodiments, the surface of the mannitol microparticle is coated with a layer of the nanoparticles. In certain embodiments, the surface of the mannitol microparticle is substantially coated with a layer of the nanoparticles. In certain embodiments, the surface of the mannitol microparticle is coated with a single layer of the nanoparticles. In certain embodiments, the surface of the mannitol microparticle is substantially coated with a single layer of the nanoparticles.

In certain embodiments, the mannitol microparticle in the coated particle provided herein has various shapes, including, but not limited to, a sphere, spheroid, platelet, fibril, or fiber. In certain embodiments, the mannitol microparticle in the coated particle provided herein is substantially spherical. In certain embodiments, the mannitol microparticle in the coated particle provided herein is spherical. In certain embodiments, the mannitol microparticle in the coated particle provided herein is spheroidal.

In certain embodiments, the mannitol microparticle in the coated particle provided herein has an average particle size ranging from about 1 to about 1,000 μm, from about 10 to about 500 μm, from about 20 to about 500 μm, from about 50 to about 300 μm, or from about 100 to about 300 μm. In certain embodiments, the mannitol microparticle in the coated particle provided herein has an average particle size ranging from about 1 to about 1,000 μm. In certain embodiments, the mannitol microparticle in the coated particle provided herein has an average particle size ranging from about 10 to about 500 μm. In certain embodiments, the mannitol microparticle in the coated particle provided herein has an average particle size ranging from about 20 to about 500 μm. In certain embodiments, the mannitol microparticle in the coated particle provided herein has an average particle size ranging from about 50 to about 300 μm. In certain embodiments, the mannitol microparticle in the coated particle provided herein has an average particle size ranging from about 100 to about 300 μm. In certain embodiments, the mannitol microparticle in the coated particle provided herein has an average particle size of about 50, about 100, about 150, about 200, about 250, about 300, about 350, about 400, about 450, or about 500 μm.

In certain embodiments, the mannitol microparticle in the coated particle provided herein has an average particle size ranging from about 1 to about 100 μm, from about 1 to about 50 μm, or from about 1 to about 25 μm. In certain embodiments, the mannitol microparticle in the coated particle provided herein has an average particle size ranging from about 1 to about 100 μm. In certain embodiments, the mannitol microparticle in the coated particle provided herein has an average particle size ranging from about 1 to about 50 μm. In certain embodiments, the mannitol microparticle in the coated particle provided herein has an average particle size ranging from about 1 to about 25 μm. In certain embodiments, the mannitol microparticle in the coated particle provided herein has an average particle size of about 5, about 10, about 15, about 20, about 25, about 30, about 35, about 40, about 45, or about 50 μm.

In yet another embodiment, provided herein is a coated particle comprising: (i) a microparticle that comprises D-dextrose and (ii) nanoparticles, each comprising a therapeutic agent; wherein the surface of the D-dextrose microparticle is coated with the nanoparticles.

In certain embodiments, the surface of the D-dextrose microparticle is coated with a layer of the nanoparticles. In certain embodiments, the surface of the D-dextrose microparticle is substantially coated with a layer of the nanoparticles. In certain embodiments, the surface of the D-dextrose microparticle is coated with a single layer of the nanoparticles. In certain embodiments, the surface of the D-dextrose microparticle is substantially coated with a single layer of the nanoparticles.

In certain embodiments, the D-dextrose microparticle in the coated particle provided herein has various shapes, including, but not limited to, a sphere, spheroid, platelet, fibril, or fiber. In certain embodiments, the D-dextrose microparticle in the coated particle provided herein is substantially spherical. In certain embodiments, the D-dextrose microparticle in the coated particle provided herein is spherical. In certain embodiments, the D-dextrose microparticle in the coated particle provided herein is spheroidal.

In certain embodiments, the D-dextrose microparticle in the coated particle provided herein has an average particle size ranging from about 1 to about 1,000 μm, from about 10 to about 500 μm, from about 20 to about 500 μm, from about 50 to about 300 μm, or from about 100 to about 300 μm. In certain embodiments, the D-dextrose microparticle in the coated particle provided herein has an average particle size ranging from about 1 to about 1,000 μm. In certain embodiments, the D-dextrose microparticle in the coated particle provided herein has an average particle size ranging from about 10 to about 500 μm. In certain embodiments, the D-dextrose microparticle in the coated particle provided herein has an average particle size ranging from about 20 to about 500 μm. In certain embodiments, the D-dextrose microparticle in the coated particle provided herein has an average particle size ranging from about 50 to about 300 μm. In certain embodiments, the D-dextrose microparticle in the coated particle provided herein has an average particle size ranging from about 100 to about 300 μm. In certain embodiments, the D-dextrose microparticle in the coated particle provided herein has an average particle size of about 50, about 100, about 150, about 200, about 250, about 300, about 350, about 400, about 450, or about 500 μm.

In certain embodiments, the D-dextrose microparticle in the coated particle provided herein has an average particle size ranging from about 1 to about 100 μm, from about 1 to about 50 μm, or from about 1 to about 25 μm. In certain embodiments, the D-dextrose microparticle in the coated particle provided herein has an average particle size ranging from about 1 to about 100 μm. In certain embodiments, the D-dextrose microparticle in the coated particle provided herein has an average particle size ranging from about 1 to about 50 μm. In certain embodiments, the D-dextrose microparticle in the coated particle provided herein has an average particle size ranging from about 1 to about 25 μm. In certain embodiments, the D-dextrose microparticle in the coated particle provided herein has an average particle size of about 5, about 10, about 15, about 20, about 25, about 30, about 35, about 40, about 45, or about 50 μm.

In certain embodiments, the coated particle containing D-dextrose is formulated as a sterile solid for reconstitution.

In certain embodiments, the therapeutic agent in the coated particle provided herein is a class II compound according to the Biopharmaceutics Classification System (BCS), i.e., a BCS class II compound. In certain embodiments, the therapeutic agent in the coated particle provided herein is a BCS class III compound. In certain embodiments, the therapeutic agent in the coated particle provided herein is a BCS class IV compound.

In certain embodiments, the therapeutic agent in the coated particle provided herein has a low solubility to the Biopharmaceutics Classification System. In certain embodiments, the therapeutic agent in the coated particle provided herein has a low permeability to the Biopharmaceutics Classification System.

In certain embodiments, the therapeutic agent in the coated particle provided herein is a solid. In certain embodiments, the therapeutic agent in the coated particle provided herein has a melting point ranging from about 50 to about 500° C., from about 100 to about 400° C., from about 100 to about 300° C., or from about 150 to about 300° C. In certain embodiments, the therapeutic agent in the coated particle provided herein has a melting point ranging from about 50 to about 500° C. In certain embodiments, the therapeutic agent in the coated particle provided herein has a melting point ranging from about 100 to about 400° C. In certain embodiments, the therapeutic agent in the coated particle provided herein has a melting point ranging from about 100 to about 300° C. In certain embodiments, the therapeutic agent in the coated particle provided herein has a melting point ranging from about 150 to about 300° C.

In certain embodiments, the therapeutic agent in the coated particle provided herein is amiodarone, atorvastatin, azithromycin, carbamazepine, carvedilol, chlorpromazine, cisapride, ciprofloxacin, cloxacillin, cyclosporine, danazol, dapsone, diclofenac, diflunisal, digoxin, erythromycin, fenofibrate, flurbiprofen, glipizide, glyburide, griseofulvin, hydroxyzine, ibuprofen, indinavir, indomethacin, itraconazole, ivermectin, ketoconazole, ketoprofen, lansoprazole, lovastatin, mebendazole, midazolam, naproxen, nelfinavir, niclosamide, ofloxacin, oxaprozin, phenazopyridine, phenytoin, piroxicam, praziquantel, raloxifene, ritonavir, saquinavir, sirolimus, spironolactone, tacrolimus, talinolol, tamoxifen, terfenadine, or warfarin.

In certain embodiments, the therapeutic agent in the coated particle provided herein is amlodipine, amoxicillin, cimetidine, ciprofloxacin, ethosuximide, metronidazole, morphine, paracetamol, phenoxymethylpenicillin, or procainamide.

In certain embodiments, the therapeutic agent in the coated particle provided herein is amoxicillin, amphotericin B, cefalexin, chloramphenicol, chlorthalidone, chlorothiazide, ciprofloxacin, clindamycin, colistin, furosemide, hydrochlorothiazide, mebendazole, meloxicam, methotrexate, neomycin, nitrofurantoin, oxamniquine, phenobarbital, prednisolone, sulfamethoxazole, or trimethoprim.

In certain embodiments, the therapeutic agent in the coated particle provided herein is arformoterol, asenapine, dabigatran, desonide, dexlansoprazole, diclofenac, efavirenz, emtricitabine, erlotinib, fesoterodine, formoterol, isotretinoin, lacosamide, lenalidomide, lubiprostone, maraviroc, mesalamine, nebivolol, posaconazole, roflumilast, sitagliptin, sunitinib, tenofovir, ticagrelor, varenicline, or vilazodone.

In certain embodiments, the therapeutic agent in the coated particle provided herein is cannabidiol, carbamazepine, ibuprofen, nifedipine, piroxicam, plumbagin, verapamil, or zileuton. In certain embodiments, the therapeutic agent in the coated particle provided herein is cannabidiol, ibuprofen, or nifedipine. In certain embodiments, the therapeutic agent in the coated particle provided herein is cannabidiol. In certain embodiments, the therapeutic agent in the coated particle provided herein is carbamazepine. In certain embodiments, the therapeutic agent in the coated particle provided herein is ibuprofen. In certain embodiments, the therapeutic agent in the coated particle provided herein is nifedipine. In certain embodiments, the therapeutic agent in the coated particle provided herein is piroxicam. In certain embodiments, the therapeutic agent in the coated particle provided herein is plumbagin. In certain embodiments, the therapeutic agent in the coated particle provided herein is verapamil. In certain embodiments, the therapeutic agent in the coated particle provided herein is zileuton.

In certain embodiments, the nanoparticles in the coated particle provided herein have an average particle size ranging from about 1 to about 500 nm, from about 1 to about 200 nm, from about 2 to about 200 nm, from about 5 to about 200 nm, from about 10 to about 200 nm, or from about 10 to about 100 nm. In certain embodiments, the nanoparticles in the coated particle provided herein have an average particle size ranging from about 1 to about 500 nm. In certain embodiments, the nanoparticles in the coated particle provided herein have an average particle size ranging from about 1 to about 200 nm. In certain embodiments the nanoparticles in the coated particle provided herein have an average particle size ranging from about 1 to about 50 nm. In certain embodiments, the nanoparticles in the coated particle provided herein have an average particle size ranging from about 2 to about 200 nm. In certain embodiments, the nanoparticles in the coated particle provided herein have an average particle size ranging from about 5 to about 200 nm. In certain embodiments, the nanoparticles in the coated particle provided herein have an average particle size ranging from about 10 to about 200 nm. In certain embodiments, the nanoparticles in the coated particle provided herein have an average particle size ranging from about 10 to about 100 nm.

In certain embodiments, the nanoparticles in the coated particle provided herein have an average particle size ranging from about 10 to about 500 nm, from about 10 to about 200 nm, or from about 20 to about 200 nm. In certain embodiments, the nanoparticles in the coated particle provided herein have an average particle size ranging from about 10 to about 500 nm. In certain embodiments, the nanoparticles in the coated particle provided herein have an average particle size ranging from about 10 to about 200 nm. In certain embodiments the nanoparticles in the coated particle provided herein have an average particle size ranging from about 20 to about 200 nm. In certain embodiments, the nanoparticles in the coated particle provided herein have an average particle size of about 10, about 20, about 30, about 40, or about 50 nm. In certain embodiments, the nanoparticles in the coated particle provided herein have an average particle size of about 100, about 150, about 200, about 250, about 300, about 350, about 400, about 450, or about 500 nm.

In certain embodiments, the nanoparticles in the coated particle provided herein are formed on the surface of the microparticle. In certain embodiments, the nanoparticles in the coated particle provided herein are formed on the surface of the microparticle by organic vapor phase deposition. See, e.g., Baldo et al., *Adv. Mater.* 1998, 10, 1505-1514.

In certain embodiments, the percentage of the nanoparticles in the coated particle is ranging from about 0.1 to about 25% by weight, about 0.2 to about 20% by weight, about 0.5 to about 10% by weight, or about 1 to about 10% by weight. In certain embodiments, the percentage of the nanoparticles in the coated particle is ranging from about 0.1 to about 25% by weight. In certain embodiments, the percentage of the nanoparticles in the coated particle is ranging from about 0.2 to about 20% by weight. In certain embodiments, the percentage of the nanoparticles in the coated particle is ranging from about 0.5 to about 10% by weight. In certain embodiments, the percentage of the nanoparticles in the coated particle is ranging from about 1 to about 10% by weight. In certain embodiments, the percentage of the nanoparticles in the coated particle is about 1, about 2, about 3, about 4, about 5, about 6, about 7, about 8, about 9, or about 10% by weight.

In certain embodiments, the coated particle provided herein has an average particle size ranging from about 1 to about 1,000 μm, from about 10 to about 500 μm, from about 20 to about 500 μm, from about 50 to about 300 μm, or from about 100 to about 300 μm. In certain embodiments, the coated particle provided herein has an average particle size ranging from about 1 to about 1,000 μm. In certain embodiments, the coated particle provided herein has an average particle size ranging from about 10 to about 500 μm. In certain embodiments, the coated particle provided herein has an average particle size ranging from about 20 to about 500 μm. In certain embodiments, the coated particle provided herein has an average particle size ranging from about 50 to about 300 μm. In certain embodiments, the coated particle provided herein has an average particle size ranging from about 100 to about 300 μm. In certain embodiments, the coated particle provided herein has an average particle size of about 50, about 100, about 150, about 200, about 250, about 300, about 350, about 400, about 450, or about 500 μm.

In certain embodiments, the coated particle provided herein has an average particle size ranging from about 1 to about 100 μm, from about 1 to about 50 μm, or from about 1 to about 25 μm. In certain embodiments, the coated particle provided herein has an average particle size ranging from about 1 to about 100 μm. In certain embodiments, the coated particle provided herein has an average particle size ranging from about 1 to about 50 μm. In certain embodiments, the coated particle provided herein has an average particle size ranging from about 1 to about 25 μm. In certain embodiments, the coated particle provided herein has an average particle size of about 5, about 10, about 15, about 20, about 25, about 30, about 35, about 40, about 45, or about 50 μm.

Method of Preparation

In one embodiment, provided herein is a method of preparing coated particles, each particle comprising: (i) a microparticle that comprises a pharmaceutically acceptable excipient and (ii) nanoparticles of a therapeutic agent, comprising the steps of:
  a. vaporizing the therapeutic agent at a first predetermined temperature under a predetermined vacuum pressure to form a vapor; and
  b. depositing the vapor on the surface of the microparticle at a predetermined agitation speed and a second predetermined temperature under the predetermined vacuum pressure to form the nanoparticles on the surfaces of the microparticles, thus forming the coated particles.

In another embodiment, provided herein is a method of preparing nanoparticles of a therapeutic agent, comprising the steps of:
  a. vaporizing the therapeutic agent at a first predetermined temperature under a predetermined vacuum pressure to form a vapor; and
  b. depositing the vapor on the surface of a microparticle comprising a pharmaceutically acceptable excipient at a predetermined agitation speed and a second predetermined temperature under the predetermined vacuum pressure to form the nanoparticles on the surface of the microparticle.

In certain embodiments, the first predetermined temperature is ranging from about 50 to about 500° C., from about 100 to about 400° C., from about 50 to about 300° C., from about 100 to about 300° C., from about 100 to about 250° C., from about 150 to about 300° C., or from about 200 to about 300° C. In certain embodiments, the first predetermined temperature is ranging from about 50 to about 500° C. In certain embodiments, the first predetermined temperature is ranging from about 100 to about 400° C. In certain embodiments, the first predetermined temperature is ranging from about 50 to about 300° C. In certain embodiments, the first predetermined temperature is ranging from about 100 to about 300° C. In certain embodiments, the first predetermined temperature is ranging from about 100 to about 250° C. In certain embodiments, the first predetermined temperature is ranging from about 150 to about 300° C. In certain embodiments, the first predetermined temperature is ranging from about 200 to about 300° C. In certain embodiments, the first predetermined temperature is about 150, about 175, about 200, about 250, about 250, about 275, or about 300° C.

In certain embodiments, the first predetermined temperature is ranging from about 50 to about 250° C., from about 80 to about 250° C., or from about 100 to about 250° C. In certain embodiments, the first predetermined temperature is ranging from about 50 to about 250° C. In certain embodiments, the first predetermined temperature is ranging from about 80 to about 250° C. In certain embodiments, the first predetermined temperature is ranging from about 100 to about 250° C. In certain embodiments, the first predetermined temperature is about 80, about 90, about 100, about 125, about 150, about 175, about 200, about 225, or about 250° C.

In certain embodiments, the predetermined vacuum pressure is no greater than about $10^{-1}$ torr, no greater than about $10^{-2}$ torr, no greater than about $10^3$ torr, no greater than about $10^4$ torr, no greater than about $10^{-5}$ torr, no greater than about $10^6$ torr, no greater than about $10^{-7}$ torr, no greater than about $10^{-8}$ torr, or no greater than about $10^{-9}$ torr. In certain embodiments, the first predetermined vacuum pressure is no greater than about $10^{-1}$ torr. In certain embodiments, the predetermined vacuum pressure is no greater than about $10^{-2}$ torr. In certain embodiments, the predetermined vacuum pressure is no greater than about $10^3$ torr. In certain embodiments, the first predetermined vacuum pressure is no greater than about $10^{-4}$ torr. In certain embodiments, the predetermined vacuum pressure is no greater than about $10_5$ torr. In certain embodiments, the predetermined vacuum pressure is no greater than about $10^{-6}$ torr. In certain embodiments, the first predetermined vacuum pressure is no greater than about $10^{-7}$ torr. In certain embodiments, the predetermined vacuum pressure is no greater than about $10^{-8}$ torr. In certain embodiments, the predetermined vacuum pressure is no greater than about $10^{-9}$ torr. In certain embodiments, the predetermined vacuum pressure is about $10^{-3}$, about $10^4$, about $10^{-5}$, about $10^{-6}$, about $10^{-7}$, about $10^{-8}$, or about $10^{-9}$ torr.

In certain embodiments, the predetermined vacuum pressure is ranging from about $10^{-3}$ to about $10^{-9}$ torr. In certain embodiments, the predetermined vacuum pressure is ranging from about $10^{-3}$ to about $10^{-6}$ torr. In certain embodiments, the predetermined vacuum pressure is ranging from about $10^{-3}$ to about $10^{-4}$ torr. In certain embodiments, the predetermined vacuum pressure is ranging from about $10^{-4}$ to about $10^{-8}$ torr. In certain embodiments, the predetermined vacuum pressure is ranging from about $10^{-4}$ to about $10^{-7}$ torr. In certain embodiments, the predetermined vacuum pressure is ranging from about $10^{4}$ to about $10^{-6}$ torr.

In certain embodiments, the predetermined agitation speed is ranging from about 10 to about 200 revolutions per minute (rpm), from about 20 to about 150 rpm, from about 20 to about 120 rpm, from about 20 to about 100 rpm, from about 50 to about 100 rpm, or from about 80 to about 100 rpm. In certain embodiments, the predetermined agitation speed is ranging from about 10 to about 200 rpm. In certain embodiments, the predetermined agitation speed is ranging from about 20 to about 150 rpm. In certain embodiments, the predetermined agitation speed is ranging from about 20 to about 120 rpm. In certain embodiments, the predetermined agitation speed is ranging from about 20 to about 100 rpm. In certain embodiments, the predetermined agitation speed is ranging from about 50 to about 100 rpm. In certain embodiments, the predetermined agitation speed is ranging from about 80 to about 100 rpm. In certain embodiments, the predetermined agitation speed is about 80, about 85, about 90, about 95, or about 100 rpm.

To efficiently deposit the vapor of a therapeutic agent onto the surface of a microparticle of a pharmaceutically acceptable excipient, the second predetermined temperature is set to be lower than the first predetermined temperature. Thus, the second predetermined temperature is no less than about 10, about no less than about 20, no less than about 50, or no less than about 100° C. lower than the first predetermined temperature.

In certain embodiments, the second predetermined temperature is no greater than about 100° C., no greater than about 50° C., no greater than about 40° C., no greater than about 35° C., no greater than about 30° C., or no greater than about 25° C. In certain embodiments, the second predetermined temperature is no greater than about 100° C. In certain embodiments, the second predetermined temperature is no greater than about 50° C. In certain embodiments, the second predetermined temperature is no greater than about 40° C. In certain embodiments, the second predetermined temperature is no greater than about 35° C. In certain embodiments, the second predetermined temperature is no greater than about 30° C. In certain embodiments, the second predetermined temperature is no greater than about 25° C.

In certain embodiments, the second predetermined temperature is ranging from about 10 to about 100° C., from about 15 to about 50° C., or from about 20 to about 40° C. In certain embodiments, the second predetermined temperature is ranging from about 10 to about 100° C. In certain embodiments, the second predetermined temperature is ranging from about 15 to about 50° C. In certain embodiments, the second predetermined temperature is ranging from about 20 to about 40° C. In certain embodiments, the second predetermined temperature is about 20, about 25, about 30, about 35, or about 40° C. In certain embodiments, the second predetermined temperature is ambient temperature.

Thus, in one embodiment, provided herein are coated particles, each particle comprising: (i) a microparticle that comprises a pharmaceutically acceptable excipient and (ii) nanoparticles of a therapeutic agent; wherein the coated particles are prepared by a method comprising the steps of:
  a. vaporizing the therapeutic agent at the first predetermined temperature under the predetermined vacuum pressure to form a vapor; and
  b. depositing the vapor on the surface of the microparticle at the predetermined agitation speed and the second predetermined temperature under the predetermined vacuum pressure to form the nanoparticles on the surfaces of the microparticles, thus forming the coated particles.

In another embodiment, provided herein are nanoparticles of a therapeutic agent, which are prepared by a method comprising the steps of:
  a. vaporizing the therapeutic agent at the first predetermined temperature under the predetermined vacuum pressure to form a vapor; and
  b. depositing the vapor on the surface of a microparticle comprising a pharmaceutically acceptable excipient at the predetermined agitation speed and the second predetermined temperature under the predetermined vacuum pressure to form the nanoparticles on the surface of the microparticle.

In yet another embodiment, provided herein is a batch of coated particles, each particle comprising: (i) a microparticle that comprises a pharmaceutically acceptable excipient and (ii) nanoparticles of a therapeutic agent; wherein the coated particles are prepared by a method comprising the steps of:
  a. vaporizing the therapeutic agent at the first predetermined temperature under the predetermined vacuum pressure to form a vapor; and
  b. depositing the vapor on the surface of the microparticle at the predetermined agitation speed and the second predetermined temperature under the predetermined vacuum pressure to form the nanoparticles on the surfaces of the microparticles, thus forming the coated particles.

In still another embodiment, provided herein is a batch of nanoparticles of a therapeutic agent, which are prepared by a method comprising the steps of:
  a. vaporizing the therapeutic agent at the first predetermined temperature under the predetermined vacuum pressure to form a vapor; and
  b. depositing the vapor on the surface of a microparticle comprising a pharmaceutically acceptable excipient at the predetermined agitation speed and the second predetermined temperature under the predetermined vacuum pressure to form the nanoparticles on the surface of the microparticle.

In one embodiment, provided herein are coated particles, each particle comprising: (i) a mannitol microparticle and (ii) nanoparticles of a therapeutic agent; wherein the coated particles are prepared by a method comprising the steps of:
  a. vaporizing the therapeutic agent at the first predetermined temperature under the predetermined vacuum pressure to form a vapor; and
  b. depositing the vapor on the surfaces of the mannitol microparticles at the predetermined agitation speed and the second predetermined temperature under the predetermined vacuum pressure to form the nanoparticles on the surfaces of the mannitol microparticles, thus forming the coated particles.

In another embodiment, provided herein are nanoparticles of a therapeutic agent, which are prepared by a method comprising the steps of:
  a. vaporizing the therapeutic agent at the first predetermined temperature under the predetermined vacuum pressure to form a vapor; and
  b. depositing the vapor on the surface of a mannitol microparticle at the predetermined agitation speed and the second predetermined temperature under the predetermined vacuum pressure to form the nanoparticles on the surface of the mannitol microparticle.

In yet another embodiment, provided herein is a batch of coated particles, each particle comprising: (i) a mannitol microparticle and (ii) nanoparticles of a therapeutic agent; wherein the coated particles are prepared by a method comprising the steps of:
 a. vaporizing the therapeutic agent at the first predetermined temperature under the predetermined vacuum pressure to form a vapor; and
 b. depositing the vapor on the surfaces of the mannitol microparticles at the predetermined agitation speed and the second predetermined temperature under the predetermined vacuum pressure to form the nanoparticles on the surfaces of the mannitol microparticles, thus forming the coated particles.

In still another embodiment, provided herein is a batch of nanoparticles of a therapeutic agent, which are prepared by a method comprising the steps of:
 a. vaporizing the therapeutic agent at the first predetermined temperature under the predetermined vacuum pressure to form a vapor; and
 b. depositing the vapor on the surface of a mannitol microparticle at the predetermined agitation speed and the second predetermined temperature under the predetermined vacuum pressure to form the nanoparticles on the surface of the mannitol microparticle.

In one embodiment, provided herein are coated particles, each particle comprising: (i) a D-dextrose microparticle and (ii) nanoparticles of a therapeutic agent; wherein the coated particles are prepared by a method comprising the steps of:
 a. vaporizing the therapeutic agent at the first predetermined temperature under the predetermined vacuum pressure to form a vapor; and
 b. depositing the vapor on the surfaces of the D-dextrose microparticles at the predetermined agitation speed and the second predetermined temperature under the predetermined vacuum pressure to form the nanoparticles on the surfaces of the D-dextrose microparticles, thus forming the coated particles.

In another embodiment, provided herein are nanoparticles of a therapeutic agent, which are prepared by a method comprising the steps of:
 a. vaporizing the therapeutic agent at the first predetermined temperature under the predetermined vacuum pressure to form a vapor; and
 b. depositing the vapor on the surface of a D-dextrose microparticle at the predetermined agitation speed and the second predetermined temperature under the predetermined vacuum pressure to form the nanoparticles on the surface of the D-dextrose microparticle.

In yet another embodiment, provided herein is a batch of coated particles, each particle comprising: (i) a D-dextrose microparticle and (ii) nanoparticles of a therapeutic agent; wherein the coated particles are prepared by a method comprising the steps of:
 a. vaporizing the therapeutic agent at the first predetermined temperature under the predetermined vacuum pressure to form a vapor; and
 b. depositing the vapor on the surfaces of the D-dextrose microparticles at the predetermined agitation speed and the second predetermined temperature under the predetermined vacuum pressure to form the nanoparticles on the surfaces of the D-dextrose microparticles, thus forming the coated particles.

In still another embodiment, provided herein is a batch of nanoparticles of a therapeutic agent, which are prepared by a method comprising the steps of:
 a. vaporizing the therapeutic agent at the first predetermined temperature under the predetermined vacuum pressure to form a vapor; and
 b. depositing the vapor on the surface of a D-dextrose microparticle at the predetermined agitation speed and the second predetermined temperature under the predetermined vacuum pressure to form the nanoparticles on the surface of the D-dextrose microparticle.

Pharmaceutical Compositions

In one embodiment, provided herein is a pharmaceutical composition comprising coated particles, each particle comprising: (i) a microparticle that comprises a pharmaceutically acceptable excipient and (ii) nanoparticles of a therapeutic agent, wherein the surface of the microparticle is coated with the nanoparticles.

In another embodiment, provided herein is a pharmaceutical composition comprising coated particles, each particle comprising: (i) a microparticle that comprises a pharmaceutically acceptable excipient and (ii) nanoparticles of a therapeutic agent; wherein the coated particles are prepared by a method comprising the steps of:
 a. vaporizing the therapeutic agent at a first predetermined temperature under a predetermined vacuum pressure to form a vapor; and
 b. depositing the vapor on the surfaces of the microparticles at a predetermined agitation speed and a second predetermined temperature under the predetermined vacuum pressure to form the nanoparticles on the surfaces of the microparticles, thus forming the coated particles.

In yet another embodiment, provided herein is a pharmaceutical composition comprising nanoparticles of a therapeutic agent, which are prepared by a method comprising the steps of:
 a. vaporizing the therapeutic agent at a first predetermined temperature under a predetermined vacuum pressure to form a vapor; and
 b. depositing the vapor on the surface of a microparticle comprising a pharmaceutically acceptable excipient at a predetermined agitation speed and a second predetermined temperature under the predetermined vacuum pressure to form the nanoparticles on the surface of the microparticle.

In yet another embodiment, provided herein is a batch of a pharmaceutical composition comprising coated particles, each particle comprising: (i) a microparticle that comprises a pharmaceutically acceptable excipient and (ii) nanoparticles of a therapeutic agent; wherein the coated particles are prepared by a method comprising the steps of:
 a. vaporizing the therapeutic agent at a first predetermined temperature under a predetermined vacuum pressure to form a vapor; and
 b. depositing the vapor on the surfaces of the microparticles at a predetermined agitation speed and a second predetermined temperature under the predetermined vacuum pressure to form the nanoparticles on the surfaces of the microparticles, thus forming the coated particles.

In still another embodiment, provided herein is a batch of a pharmaceutical composition comprising nanoparticles of a therapeutic agent and a pharmaceutical acceptable excipient, wherein the nanoparticles are prepared by a method comprising the steps of:

a. vaporizing the therapeutic agent at a predetermined temperature under a first predetermined vacuum pressure to form a vapor; and b. depositing the vapor on the surface of a microparticle comprising the pharmaceutically acceptable excipient at a predetermined agitation speed and a second predetermined temperature under the predetermined vacuum pressure to form the nanoparticles on the surface of the microparticle.

In one embodiment, provided herein is a pharmaceutical composition comprising coated particles, each particle comprising: (i) a mannitol microparticle and (ii) nanoparticles of a therapeutic agent, wherein the surface of the mannitol microparticle is coated with the nanoparticles.

In another embodiment, provided herein is a pharmaceutical composition comprising coated particles, each particle comprising: (i) a mannitol microparticle and (ii) nanoparticles of a therapeutic agent; wherein the coated particles are prepared by a method comprising the steps of:

a. vaporizing the therapeutic agent at a first predetermined temperature under a predetermined vacuum pressure to form a vapor; and b. depositing the vapor on the surfaces of the mannitol microparticles at a predetermined agitation speed and a second predetermined temperature under the predetermined vacuum pressure to form the nanoparticles on the surfaces of the mannitol microparticles, thus forming the coated particles.

In yet another embodiment, provided herein is a pharmaceutical composition comprising nanoparticles of a therapeutic agent, which are prepared by a method comprising the steps of:

a. vaporizing the therapeutic agent at a first predetermined temperature under a predetermined vacuum pressure to form a vapor; and b. depositing the vapor on the surface of a mannitol microparticle comprising a pharmaceutically acceptable excipient at a predetermined agitation speed and a second predetermined temperature under the predetermined vacuum pressure to form the nanoparticles on the surface of the mannitol microparticle.

In yet another embodiment, provided herein is a batch of a pharmaceutical composition comprising coated particles, each particle comprising: (i) a mannitol microparticle and (ii) nanoparticles of a therapeutic agent; wherein the coated particles are prepared by a method comprising the steps of:

a. vaporizing the therapeutic agent at a first predetermined temperature under a predetermined vacuum pressure to form a vapor; and b. depositing the vapor on the surfaces of the mannitol microparticles at a predetermined agitation speed and a second predetermined temperature under the predetermined vacuum pressure to form the nanoparticles on the surfaces of the mannitol microparticles, thus forming the coated particles.

In still another embodiment, provided herein is a batch of a pharmaceutical composition comprising nanoparticles of a therapeutic agent and a pharmaceutical acceptable excipient, wherein the nanoparticles are prepared by a method comprising the steps of:

a. vaporizing the therapeutic agent at a predetermined temperature under a first predetermined vacuum pressure to form a vapor; and b. depositing the vapor on the surface of a mannitol microparticle comprising the pharmaceutically acceptable excipient at a predetermined agitation speed and a second predetermined temperature under the predetermined vacuum pressure to form the nanoparticles on the surface of the mannitol microparticle.

In one embodiment, provided herein is a pharmaceutical composition comprising coated particles, each particle comprising: (i) a D-dextrose microparticle and (ii) nanoparticles of a therapeutic agent, wherein the surface of the D-dextrose microparticle is coated with the nanoparticles.

In another embodiment, provided herein is a pharmaceutical composition comprising coated particles, each particle comprising: (i) a D-dextrose microparticle and (ii) nanoparticles of a therapeutic agent; wherein the coated particles are prepared by a method comprising the steps of:

a. vaporizing the therapeutic agent at a first predetermined temperature under a predetermined vacuum pressure to form a vapor; and b. depositing the vapor on the surfaces of the D-dextrose microparticles at a predetermined agitation speed and a second predetermined temperature under the predetermined vacuum pressure to form the nanoparticles on the surfaces of the D-dextrose microparticles, thus forming the coated particles.

In yet another embodiment, provided herein is a pharmaceutical composition comprising nanoparticles of a therapeutic agent, which are prepared by a method comprising the steps of:

a. vaporizing the therapeutic agent at a first predetermined temperature under a predetermined vacuum pressure to form a vapor; and b. depositing the vapor on the surface of a D-dextrose microparticle comprising a pharmaceutically acceptable excipient at a predetermined agitation speed and a second predetermined temperature under the predetermined vacuum pressure to form the nanoparticles on the surface of the D-dextrose microparticle.

In yet another embodiment, provided herein is a batch of a pharmaceutical composition comprising coated particles, each particle comprising: (i) a D-dextrose microparticle and (ii) nanoparticles of a therapeutic agent; wherein the coated particles are prepared by a method comprising the steps of:

a. vaporizing the therapeutic agent at a first predetermined temperature under a predetermined vacuum pressure to form a vapor; and b. depositing the vapor on the surfaces of the D-dextrose microparticles at a predetermined agitation speed and a second predetermined temperature under the predetermined vacuum pressure to form the nanoparticles on the surfaces of the D-dextrose microparticles, thus forming the coated particles.

In still another embodiment, provided herein is a batch of a pharmaceutical composition comprising nanoparticles of a therapeutic agent and a pharmaceutical acceptable excipient, wherein the nanoparticles are prepared by a method comprising the steps of:

a. vaporizing the therapeutic agent at a predetermined temperature under a first predetermined vacuum pressure to form a vapor; and b. depositing the vapor on the surface of a D-dextrose microparticle comprising the pharmaceutically acceptable excipient at a predetermined agitation speed and a second predetermined temperature under the predetermined vacuum pressure to form the nanoparticles on the surface of the D-dextrose microparticle.

The pharmaceutical compositions provided herein can each independently be formulated in various dosage forms, including, but not limited to, dosage forms for oral, parenteral, and topical administration. The pharmaceutical compositions can also each independently be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art. See, e.g., *Remington: The Science and Practice of Pharmacy, supra; Modified-Release Drug Delivery Technology,* 2nd ed.; Rathbone et al., Eds.; Drugs and the Pharmaceutical Sciences 184; CRC Press: Boca Raton, FL, 2008.

In one embodiment, a pharmaceutical composition provided herein is formulated in a dosage form for oral administration. In another embodiment, a pharmaceutical composition provided herein is formulated in a dosage form for parenteral administration. In yet another embodiment, a pharmaceutical composition provided herein is formulated in a dosage form for topical administration.

In one embodiment, a pharmaceutical composition provided herein is formulated in a sterile solid dosage form for reconstitution for parenteral administration. In another embodiment, a pharmaceutical composition provided herein is formulated in a solid dosage form for reconstitution for intravenous administration. In yet another embodiment, a pharmaceutical composition provided herein is formulated in a solid dosage form for reconstitution for intramuscular administration. In still another embodiment, a pharmaceutical composition provided herein is formulated in a solid dosage form for reconstitution for subcutaneous administration.

In certain embodiments, a pharmaceutical composition provided herein is formulated in a nonsterile solid dosage. In certain embodiments, a pharmaceutical composition provided herein is formulated in a nonsterile solid dosage form for auricular, cutaneous, gingival, nasal, ophthalmic, oral, oromucosal, rectal, transdermal, or vaginal administration, or administration by inhalation. In certain embodiments, a pharmaceutical composition provided herein is formulated in a nonsterile solid dosage form for ophthalmic or oral administration, or administration by inhalation.

The pharmaceutical compositions provided herein can each independently be provided in a unit-dosage form or multiple-dosage form. A unit-dosage form, as used herein, refers to physically discrete a unit suitable for administration to a subject, and packaged individually as is known in the art. Each unit-dose contains a predetermined quantity of an active ingredient(s) (e.g., a compound provided herein) sufficient to produce the desired therapeutic effect, in association with the required pharmaceutical excipient(s). Examples of a unit-dosage form include, but are not limited to, an ampoule, syringe, and individually packaged tablet and capsule. A unit-dosage form may be administered in fractions or multiples thereof. A multiple-dosage form is a plurality of identical unit-dosage forms packaged in a single container to be administered in a segregated unit-dosage form. Examples of a multiple-dosage form include, are not limited to, a vial, bottle of tablets or capsules, or bottle of pints or gallons.

The pharmaceutical compositions provided herein can each independently be administered at once or multiple times at intervals of time. It is understood that the precise dosage and duration of treatment may vary with the age, weight, and condition of the subject being treated, and may be determined empirically using known testing protocols or by extrapolation from in vivo or in vitro test or diagnostic data. It is further understood that for any particular individual, specific dosage regimens should be adjusted over time according to the subject's need and the professional judgment of the person administering or supervising the administration of the pharmaceutical composition.

A. Oral Administration

The pharmaceutical composition provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical composition can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500®); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), VEEGUM®, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); and microcrystalline celluloses, such as AVICEL® PH-101, AVICEL® PH-103, AVICEL® PH-105, and AVICEL® RC-581. Suitable fillers include, but are not limited to, talc, calcium carbonate, microcrystalline cellulose, powdered cellulose, dextrates, kaolin, mannitol, silicic acid, sorbitol, starch, and pre-gelatinized starch. The amount of a binder or filler in the pharmaceutical composition provided herein varies upon the type of formulation, and is readily discernible to those of ordinary skill in the art. The binder or filler may be present from about 50 to about 99% by weight in the pharmaceutical composition provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical composition provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and VEEGUM® HV; citrus pulp; cross-linked celluloses, such as croscarmellose; cross-linked polymers, such as crospovidone; cross-linked starches; calcium carbonate;

microcrystalline cellulose, such as sodium starch glycolate; polacrilin potassium; starches, such as corn starch, potato starch, tapioca starch, and pre-gelatinized starch; clays; and algins. The amount of a disintegrant in the pharmaceutical composition provided herein varies upon the type of formulation, and is readily discernible to those of ordinary skill in the art. The pharmaceutical composition provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, such as peanut oil, cottonseed oil, sunflower oil, sesame oil, olive oil, corn oil, and soybean oil; zinc stearate; ethyl oleate; ethyl laureate; agar; starch; lycopodium; and silica or silica gels, such as AEROSIL® 200 and CAB-O-SIL®. The amount of a lubricant in the pharmaceutical composition provided herein varies upon the type of formulation, and is readily discernible to those of ordinary skill in the art. The pharmaceutical compositions provided herein may contain about 0.1 to about 5% by weight of a lubricant.

Suitable glidants include, but are not limited to, colloidal silicon dioxide, CAB-O-SIL®, and asbestos-free talc. Suitable coloring agents include, but are not limited to, any of the approved, certified, water soluble FD&C dyes, and water insoluble FD&C dyes suspended on alumina hydrate, and color lakes. A color lake is a combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, VEEGUM®, acacia, sodium carbomethylcellulose, hydroxypropyl methylcellulose, and polyvinylpyrrolidone. Suitable preservatives include, but are not limited to, glycerin, methyl and propylparaben, benzoic add, and sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical composition provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredient(s) from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from an active ingredient(s) in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical composition provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient(s). The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409, 239; and 4,410,545. The capsules may also be coated as known by those of skill in the art in order to modify or sustain dissolution of the active ingredient(s).

The pharmaceutical composition provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing an active ingredient(s), and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These dosage forms can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical composition provided herein for oral administration can be also provided in the forms of liposomes, micelles, microspheres, or nanosystems. Micellar dosage forms can be prepared as described in U.S. Pat. No. 6,350,458.

The pharmaceutical composition provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the dosage forms described herein.

The pharmaceutical composition provided herein for oral administration can be formulated as immediate or modified release dosage forms, including delayed-, sustained, pulsed-, controlled, targeted-, and programmed-release forms.

B. Parenteral Administration

The pharmaceutical composition provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical composition provided herein for parenteral administration can be formulated in any dosage forms that are suitable for parenteral administration, including, but not limited to, solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science. See, e.g., *Remington: The Science and Practice of Pharmacy, supra.*

The pharmaceutical composition provided herein for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringer's injection, isotonic dextrose injection, sterile water injection, dextrose and lactated Ringer's injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants include those described herein, such as bisulfite and sodium metabisulfite. Suitable local anesthetics include, but are not limited to, procaine hydrochloride. Suitable suspending and dispersing agents include those described herein, such as sodium carboxymethylcelluose, hydroxypropyl methylcellulose, and polyvinylpyrrolidone. Suitable emulsifying agents include those described herein, such as polyoxyethylene sorbitan monolaurate, polyoxyethylene sorbitan monooleate 80, and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including «-cyclodextrin, β-cyclodextrin, hydroxypropyl-β-cyclodextrin, sulfobutylether-β-cyclodextrin, and sulfobutylether 7-β-cyclodextrin (CAPTISOL®).

When the pharmaceutical composition provided herein is formulated for multiple dosage administration, multiple dosage parenteral formulations must contain an antimicrobial agent at bacteriostatic or fungistatic concentrations. All parenteral formulations must be sterile, as known and practiced in the art.

In one embodiment, the pharmaceutical composition for parenteral administration is provided as a ready-to-use sterile solution. In another embodiment, the pharmaceutical composition is provided as a sterile dry soluble product, including a lyophilized powder and hypodermic tablet, to be reconstituted with a vehicle prior to use. In yet another embodiment, the pharmaceutical composition is provided as a ready-to-use sterile suspension. In yet another embodiment, the pharmaceutical composition is provided as a sterile dry insoluble product to be reconstituted with a vehicle prior to use. In still another embodiment, the pharmaceutical composition is provided as a ready-to-use sterile emulsion.

The pharmaceutical composition provided herein for parenteral administration can be formulated as immediate or modified release dosage forms, including delayed-, sustained, pulsed-, controlled, targeted-, and programmed-release forms.

The pharmaceutical composition provided herein for parenteral administration can be formulated as a suspension, solid, semi-solid, or thixotropic liquid, for administration as an implanted depot. In one embodiment, the pharmaceutical composition provided herein are dispersed in a solid inner matrix, which is surrounded by an outer polymeric membrane that is insoluble in body fluids but allows the active ingredient(s) in the pharmaceutical composition to diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers (such as hydrogels of esters of acrylic and methacrylic acid), collagen, cross-linked polyvinyl alcohol, and cross-linked partially hydrolyzed polyvinyl acetate.

Suitable outer polymeric membranes include, but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical composition provided herein can be administered topically to the skin, orifices, or mucosa. The topical administration, as used herein, includes (intra) dermal, conjunctival, intracorneal, intraocular, ophthalmic, auricular, transdermal, nasal, vaginal, urethral, respiratory, and rectal administration.

The pharmaceutical composition provided herein can be formulated in any dosage forms that are suitable for topical administration for local or systemic effect, including, but not limited to, emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulations of the pharmaceutical composition provided herein can also comprise liposomes, micelles, microspheres, and nanosystems.

Pharmaceutically acceptable carriers and excipients suitable for use in the topical formulations include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical composition can also be administered topically by electroporation, iontophoresis, phonophoresis, sonophoresis, or microneedle or needle-free injection, such as POWDERJECT™ and BIOJECT™.

The pharmaceutical composition provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid. See, e.g., *Remington: The Science and Practice of Pharmacy, supra*. These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical composition provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy, supra*.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with an active ingredient(s); and antioxidants as described herein, including bisulfite and sodium metabisulfite. Suitable vehicles include, but are not limited to, cocoa butter (*theobroma* oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical composition provided herein can be administered ophthalmically in the forms of solutions, suspensions, ointments, emulsions, gel-forming solutions, powders for solutions, gels, ocular inserts, and implants.

The pharmaceutical composition provided herein can be administered intranasally or by inhalation to the respiratory tract. The pharmaceutical composition can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical composition can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of an active ingredient(s); a propellant as solvent; and/or a surfactant, such as sorbitan trioleate, oleic acid, or an oligolactic acid.

The pharmaceutical composition provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical composition provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical composition provided herein for inhaled/intranasal administration can further comprise a suitable flavor, such as menthol and levomenthol; and/or sweeteners, such as saccharin and saccharin sodium.

The pharmaceutical composition provided herein for topical administration can be formulated to be immediate release or modified release, including delayed-, sustained-, pulsed-, controlled-, targeted, and programmed release.

D. Modified Release

The pharmaceutical composition provided herein can be formulated as a modified release dosage form. As used herein, the term "modified release" refers to a dosage form in which the rate or place of release of an active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical composition in modified release dosage forms can be prepared using a variety of modified release devices and methods known to those skilled in the art, including, but not limited to, matrix-controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

1. Matrix Controlled Release Devices

The pharmaceutical composition provided herein in a modified release dosage form can be fabricated using a matrix-controlled release device known to those skilled in the art. See, e.g., Takada et al. in *Encyclopedia of Controlled Drug Delivery*, Mathiowitz Ed.; Wiley, 1999; Vol. 2.

In certain embodiments, the pharmaceutical composition provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl) methacrylate, and (trimethylaminoethyl) methacrylate chloride.

In certain embodiments, the pharmaceutical composition provided herein is formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix-controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical composition provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical composition provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released, and the release rate can substantially by modulated via the thickness and porosity of the semipermeable membrane, the composition of the core, and the number, size, and position of the delivery ports.

The pharmaceutical composition in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art. See, e.g., *Remington: The Science and Practice of Pharmacy, supra*; Santus and Baker, *J. Controlled Release*, 1995, 35, 1-21; Verma et al., *Drug Dev. Ind. Pharm.*, 2000, 26, 695-708; Verma et al., *J. Controlled Release*, 2002, 79, 7-27.

In certain embodiments, the pharmaceutical composition provided herein is formulated as an AMT controlled-release dosage form, which comprises an asymmetric osmotic membrane that coats a core comprising the active ingredient(s) and other pharmaceutically acceptable excipients or carriers. See, e.g., U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical composition provided herein is formulated as an ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical composition provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, e.g., *Multiparticulate Oral Drug Delivery*; Ghebre-Sellassie Eds.; Drugs and the Pharmaceutical Sciences 65; CRC Press: 1994; and *Pharmaceutical Pelletization Technology*; Ghebre-Sellassie Eds.; Drugs and the Pharmaceutical Sciences 37; CRC Press: 1989.

Other excipients or carriers as described herein can be blended with the pharmaceutical composition to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical composition provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); mL (milliliters); μL (microliters); nm (nanometer); h (hour or hours); min (minutes); rpm (revolutions per minute); and HPLC (high performance liquid chromatography).

Unless otherwise indicated, all temperatures are expressed in ° C. (degrees Centigrade). All procedures are conducted at room temperature unless otherwise specified. Methodologies illustrated herein are intended to exemplify the applicable technologies through the use of specific examples and are not indicative of the scope of the disclosure.

Example 1

Preparation of Mannitol Microparticles Surface-Coated with Ibuprofen Nanoparticles Mannitol microparticles surface-coated with ibuprofen nanoparticles were prepared using organic vapor phase deposition (OVPD) technology. See, e.g., Baldo et al., *Adv. Mater.* 1998, 10, 1505-1514; KR 100644219B1. Ibuprofen (25 g) was loaded in a sample feed container of a nanosizer and mannitol (1,000 g) was loaded onto a coating pan. The nanosizer was conditioned to a vacuum pressure of no greater than 0.0001 torr using a vacuum pump. The sample feed chamber inside the nanosizer was heated sequentially to 100° C. for 1 h, 150° C. for 1 h, and then 200° C. for 2 h under vacuum to vaporize ibuprofen while the coating pan was agitated at 90 rpm at ambient temperature without active heating. Ibuprofen vapor coated agitated mannitol microparticles on surface upon contact to form ibuprofen nanoparticles. Upon completion, the nanosizer was pressurized to the atmospheric pressure and the coating pan was removed to collect mannitol microparticles surface-coated with ibuprofen nanoparticles. The mannitol microparticles surface-coated with ibuprofen nanoparticles thus prepared are calculated to have a drug-loading of 2% by weight.

Example 2

Preparation of Mannitol Microparticles Surface-Coated with Ibuprofen Nanoparticles Mannitol microparticles surface-coated with ibuprofen nanoparticles were prepared using the OVPD technology. Id. Ibuprofen (30 g) was loaded in a sample feed container of a nanosizer and mannitol (1,000 g) was loaded onto a coating pan. The nanosizer was conditioned to a vacuum pressure of no greater than 0.001 torr using a vacuum pump. The feed chamber inside the nanosizer was heated sequentially to 100° C. for 1 h, 150° C. for 1 h, and then 200° C. for 1 h under vacuum to vaporize ibuprofen while the coating pan was agitated at 90 rpm at ambient temperature without active heating. Ibuprofen vapor coated agitated mannitol microparticles on surface upon contact to form ibuprofen nanoparticles. Upon completion, the nanosizer was pressurized to the atmospheric pressure and the coating pan was removed to collect mannitol microparticles surface-coated with ibuprofen nanoparticles. The mannitol microparticles surface-coated with ibuprofen nanoparticles thus prepared are calculated to have a drug-loading of 2% by weight.

Example 3

In-Vitro Dissolution of Ibuprofen Nanoparticles

The in-vitro dissolution of ibuprofen nanoparticles is determined by measuring the mean dissolution profile of 6 size 00 hard gelatin capsules, each containing mannitol microparticles surface-coated with ibuprofen nanoparticles (555 mg), using the USP monograph method of ibuprofen (USP 31). The dissolution profile is measured in a pH 7.2 phosphate buffer (900 mL), using apparatus type 2 (basket) at 50 rpm and sampling at 5, 10, 15, 30, 45, and 60 min.

Example 4

Pharmacokinetics of Ibuprofen Nanoparticles in Rabbit

The pharmacokinetic profile of ibuprofen nanoparticles is determined in a rabbit using a size 00 hard gelatin capsule, which contains ibuprofen nanoparticles (50 mg) as mannitol microparticles surface-coated with ibuprofen nanoparticles (555 mg in total). The capsule is given orally, and blood is collected at 0, 0.5, 1, 2, 3, 4, 6, 8, 12, and 24 h from administration. Rabbit plasma samples (20 µL/injection) are analyzed by C18 reversed-phase HPLC coupled with a UV detector at 223 nm on a SPHERISORB® ODS2 column, eluted with acetonitrile and phosphate buffer (50:50 (v:v), pH 4.16) at the ambient temperature with a flow rate of 1.0 mL/min.

Example 5

Determination of Particle Size Distribution of Ibuprofen Nanoparticles by Light Diffraction Mannitol microparticles surface-coated with ibuprofen nanoparticles (1 g) are dissolved in water (1 mL). The resulting homogenized aqueous solution containing ibuprofen nanoparticles is analyzed for particle size distribution using a Malvern MASTERSIZER 3000 particle size analyzer. Three different samples are analyzed separately.

Example 6

Particle Size Analysis of Ibuprofen Nanoparticles by SEM

Mannitol microparticles surface-coated with ibuprofen nanoparticles (1 g) are dissolved in water (1 mL). The resulting homogenized aqueous solution containing ibuprofen nanoparticles is analyzed using scanning electron microscopy (SEM). Three different samples are analyzed separately.

Example 7

Preparation of Glucose Microparticles Surface-Coated with Ibuprofen Nanoparticles Glucose (D-dextrose) microparticles surface-coated with ibuprofen nanoparticles were prepared using the OVPD technology. Id. Ibuprofen (71 g) was loaded in a sample feed container of a nanosizer and glucose (915 g) was loaded onto a coating pan. The feed chamber inside the nanosizer was heated to 150-200° C. under $10^{-3}$ torr to vaporize ibuprofen while the coating pan was agitated at 120 rpm at ambient temperature without active heating. Ibuprofen vapor coated agitated glucose microparticles on surface upon contact to form ibuprofen nanoparticles. Upon completion, the nanosizer was pressurized to the atmospheric pressure and the coating pan was removed to collect glucose microparticles surface-coated with ibuprofen nanoparticles. The glucose microparticles surface-coated with ibuprofen nanoparticles thus prepared were calculated to have a drug-loading of 5% by weight using an assay value measured by the USP monograph method for ibuprofen (USP 31).

Example 8

Determination of Particle Size Distribution of Ibuprofen Nanoparticles on Glucose Glucose microparticles surface-coated with ibuprofen nanoparticles (250 mg) prepared in Example 7 were dissolved in water to obtain a clear suspension. The suspension was immediately used for negative staining with 2% uranyl acetate for particle size determination.

For negative staining, 100 mesh Cu formvar/carbon coated grids were glow discharged for 5 min. The freshly prepared suspension (5 µL) was incubated on the grids and allowed to adhere for 10 min. The excess suspension was wicked off with a filter paper. The grids were immediately stained twice with 2% uranyl acetate (20 µL) for 10 sec each, with wicking to remove excess between the steps. The grids were allowed to dry face down on a filter paper for a minimum of 15 min before viewing. The grids were imaged with a FEI TECNAI™ T12 TEM equipped with an AMT camera. Measurements were obtained using the AMT quantification package with the AMT camera software. The ibuprofen nanoparticles on glucose were determined twice for their particle sizes. The ibuprofen nanoparticles were determined to have an average particle size of 156±26 nm or 174±22 nm.

Example 9

Preparation of Mannitol Microparticles Surface-Coated with Ibuprofen Nanoparticles Mannitol microparticles surface-coated with ibuprofen nanoparticles were prepared using the OVPD technology. Id. Ibuprofen (26.7 g) was loaded in a sample feed container of a nanosizer and mannitol (1197 g) was loaded onto a coating pan. The feed chamber inside the nanosizer was heated to 90-130° C. under $10^{-5}$ torr to vaporize ibuprofen while the coating pan was agitated at 145 rpm at ambient temperature without active heating. Ibuprofen vapor coated agitated mannitol microparticles on surface upon contact to form ibuprofen nanoparticles. Upon completion, the nanosizer was pressurized to the atmospheric pressure and the coating pan was removed to collect mannitol microparticles surface-coated with ibuprofen nanoparticles. The mannitol microparticles surface-coated with ibuprofen nanoparticles thus prepared were calculated to have a drug-loading of 2% by weight using an assay value measured by the USP monograph method for ibuprofen (USP 31). The ibuprofen nanoparticles on mannitol were determined twice for their particle sizes using the TEM method described in Example 8. The ibuprofen nanoparticles were determined to have an average particle size of 21±4 nm or 18±3 nm.

Example 10

Preparation of Glucose Microparticles Surface-Coated with Nifedipine Nanoparticles Glucose microparticles surface-coated with nifedipine nanoparticles were prepared using the OVPD technology. Id. Nifedipine (80 g) was loaded in a sample feed container of a nanosizer and glucose (1,600 g) was loaded onto a coating pan. The feed chamber inside the nanosizer is heated to 250° C. under $10^{-3}$ torr to vaporize nifedipine while the coating pan was agitated at 120 rpm at ambient temperature without active heating. Nifedipine vapor coated agitated glucose microparticles on surface upon contact to form nifedipine nanoparticles. Upon completion, the nanosizer is pressurized to the atmospheric pressure and the coating pan was removed to collect glucose microparticles surface-coated with nifedipine nanoparticles. The glucose microparticles surface-coated with nifedipine nanoparticles thus prepared were calculated to have a drug-loading of 3% by weight using an assay value measured by the USP monograph method for nifedipine. The nifedipine nanoparticles on glucose were determined twice for their particle sizes using the TEM method described in Example 8. The nifedipine nanoparticles were determined to have an average particle size of 487±33 nm or 513±27 nm.

Example 11

Preparation of Mannitol Microparticles Surface-Coated with Cannabidiol Nanoparticles Mannitol microparticles surface-coated with cannabidiol nanoparticles were prepared using the OVPD technology. Id. Cannabidiol (26.7 g) was loaded in a sample feed container of a nanosizer and mannitol (1,197 g) was loaded onto a coating pan. The feed chamber inside the nanosizer was heated to 97-99° C. under $10^{-5}$ torr to vaporize cannabidiol while the coating pan was agitated at 145 rpm at ambient temperature without active heating. Cannabidiol vapor coated agitated mannitol microparticles on surface upon contact to form cannabidiol nanoparticles. Upon completion, the nanosizer was pressurized to the atmospheric pressure and the coating pan was removed to collect mannitol microparticles surface-coated with cannabidiol nanoparticles. The mannitol microparticles surface-coated with cannabidiol nanoparticles thus prepared were calculated to have a drug-loading of 2% by weight using an assay value measured by HPLC for cannabidiol. The cannabidiol nanoparticles on mannitol were determined twice for their particle sizes using the TEM method described in Example 8. The cannabidiol nanoparticles were determined to have an average particle size of 196±23 nm or 163±17 nm.

Example 12

Preparation of MCC Microparticles Surface-Coated with Plumbagin Nanoparticles

Microcrystalline cellulose (MCC) microparticles surface-coated with plumbagin nanoparticles are prepared using the OVPD technology. Id. Plumbagin (6 g) is loaded in a sample feed container of a nanosizer and MCC (62 g) is loaded onto a coating pan. The feed chamber inside the nanosizer is heated to 85-87° C. under $10^{-6}$ torr to vaporize plumbagin while the coating pan is agitated at 133 rpm at ambient temperature without active heating. Plumbagin vapor coats agitated MCC microparticles on surface upon contact to form plumbagin nanoparticles. Upon completion, the nanosizer is pressurized to the atmospheric pressure and the coating pan is removed to collect MCC microparticles surface-coated with plumbagin nanoparticles.

Example 13

Preparation of Lactose Microparticles Surface-Coated with Piroxicam Nanoparticles Lactose microparticles surface-coated with piroxicam nanoparticles are prepared using the OVPD technology. Id. Piroxicam (5 g) is loaded in a sample feed container of a nanosizer and lactose (120 g) is loaded onto a coating pan. The feed chamber inside the nanosizer is heated to 120-130° C. under $10^{-6}$ torr to vaporize piroxicam while the coating pan is agitated at 120 rpm at 70° C. Piroxicam vapor coats agitated lactose microparticles on surface upon contact to form piroxicam nanoparticles. Upon completion, the nanosizer is pressurized to the atmospheric pressure and the coating pan is removed to collect lactose microparticles surface-coated with piroxicam nanoparticles.

Example 14

Preparation of PVP Microparticles Surface-Coated with Zileuton Nanoparticles

Polyvinylpyrrolidone (PVP) microparticles surface-coated with zileuton nanoparticles are prepared using the OVPD technology. Id. Zileuton (7 g) is loaded in a sample feed container of a nanosizer and PVP (50 g) is loaded onto a coating pan. The feed chamber inside the nanosizer is heated to 135-147° C. under 105 torr to vaporize zileuton while the coating pan is agitated at 120 rpm at 70° C. Zileuton vapor coats agitated PVP microparticles on surface upon contact to form zileuton nanoparticles. Upon completion, the nanosizer is pressurized to the atmospheric pressure and the coating pan is removed to collect PVP microparticles surface-coated with zileuton nanoparticles.

Example 15

Preparation of HPC Microparticles Surface-Coated with Carbamazepine Nanoparticles Hydroxypropyl cellulose (HPC) microparticles surface-coated with carbamazepine nanoparticles are prepared using the OVPD technology. Id. Carbamazepine (8 g) is loaded in a sample feed container of a nanosizer and HPC (100 g) is loaded onto a coating pan. The feed chamber inside the nanosizer is heated to 189-192° C. under $10^{-6}$ torr to vaporize carbamazepine while the coating pan is agitated at 145 rpm at 70° C. Carbamazepine vapor coats agitated HPC microparticles on surface upon contact to form carbamazepine nanoparticles. Upon completion, the nanosizer is pressurized to the atmospheric pressure and the coating pan is removed to collect HPC microparticles surface-coated with carbamazepine nanoparticles.

Example 16

Preparation of HPMC Microparticles Surface-Coated with Verapamil Nanoparticles

Hydroxypropyl methylcellulose (HPMC) microparticles surface-coated with verapamil nanoparticles are prepared using the OVPD technology. Id. Verapamil (8 g) is loaded in a sample feed container of a nanosizer and HPMC (100 g) is loaded onto a coating pan. The feed chamber inside the nanosizer is heated to 130-143° C. under $10^{-6}$ torr to vaporize verapamil while the coating pan is agitated at 145 rpm at 70° C. Verapamil vapor coats agitated HPMC microparticles on surface upon contact to form verapamil nanoparticles. Upon completion, the nanosizer is pressurized to the atmospheric pressure and the coating pan is removed to collect HPMC microparticles surface-coated with verapamil nanoparticles.

The examples set forth above are provided to give those of ordinary skill in the art with a complete disclosure and description of how to make and use the claimed embodiments and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A coated particle consisting of: (i) a microparticle consisting of a pharmaceutically acceptable excipient and (ii) nanoparticles consisting of a therapeutic agent; wherein the surface of the microparticle is coated with the nanoparticles; wherein the therapeutic agent is a BCS class II or IV compound; and wherein the nanoparticles have an average particle size ranging from about 10 to about 500 nm.

2. The coated particle of claim 1, wherein the surface of the microparticle is coated with a layer of the nanoparticles.

3. The coated particle of claim 1, wherein the coated particle is prepared by a method comprising the steps of:
   a. vaporizing the therapeutic agent at a first predetermined temperature under a predetermined vacuum pressure to form a vapor; and
   b. depositing the vapor on the surface of the microparticle at a predetermined agitation speed and a second predetermined temperature under the predetermined vacuum pressure to form the nanoparticles on the surface of the microparticle, thus forming the coated particle.

4. The coated particle of claim 3, wherein the first predetermined temperature is ranging from about 50 to about 250° C.

5. The coated particle of claim 3, wherein the predetermined vacuum pressure is ranging from about $10^{-3}$ to about $10^{-9}$ torr.

6. The coated particle of claim 3, wherein the predetermined agitation speed is ranging from about 50 to about 100 rpm.

7. The coated particle of claim 3, wherein the second predetermined temperature is no greater than about 100° C.

8. The coated particle of claim 1, wherein the pharmaceutically acceptable excipient is a hydrophilic excipient.

9. The coated particle of claim 1, wherein the pharmaceutically acceptable excipient is a sugar alcohol.

10. The coated particle of claim 1, wherein the pharmaceutically acceptable excipient is a sugar.

11. The coated particle of claim 1, wherein the pharmaceutically acceptable excipient is glucose, hydroxypropyl cellulose (HPC), hydroxypropyl methylcellulose (HPMC), lactose, mannitol, or polyvinylpyrrolidone (PVP).

12. The coated particle of claim 1, wherein the microparticle has an average particle size ranging from about 1 to about 1,000 μm, from about 10 to about 500 μm, from about 20 to about 500 μm, from about 50 to about 300 μm, or from about 100 to about 300 μm.

13. The coated particle of claim 1, wherein the coated particle contains the nanoparticles in an amount ranging from about 0.1 to about 10% by weight.

14. The coated particle of claim 1, wherein the therapeutic agent is cannabidiol, carbamazepine, ibuprofen, nifedipine, piroxicam, plumbagin, verapamil, or zileuton.

15. A pharmaceutical composition comprising a coated particle of claim 1.

16. A batch of coated particles, each particle consisting of: (i) a microparticle consisting of a pharmaceutically acceptable excipient and (ii) nanoparticles consisting of a therapeutic agent; wherein the therapeutic agent is a BCS class II or IV compound; wherein the nanoparticles have an average particle size ranging from about 10 to about 500 nm; and wherein the coated particles are prepared by a method comprising the steps of:
   a. vaporizing the therapeutic agent at a first predetermined temperature under a predetermined vacuum pressure to form a vapor; and
   b. depositing the vapor on the surfaces of the microparticles at a predetermined agitation speed and a second predetermined temperature under the predetermined vacuum pressure to form the nanoparticles on the surfaces of the microparticles, thus forming the coated particles.

17. The coated particle of claim 1, wherein the pharmaceutically acceptable excipient is arabitol, erythritol, fucitol, galactitol, iditol, inositol, isomalt, lactitol, maltitol, maltotritol, mannitol, ribitol, sorbitol, threitol, volemitol, xylitol, or a mixture thereof.

18. The coated particle of claim 1, wherein the pharmaceutically acceptable excipient is mannitol.

19. The coated particle of claim 1, wherein the pharmaceutically acceptable excipient is dextrose, fructose, glucose, lactose, maltose, molasses, sucrose, trehalose, or a mixture thereof.

* * * * *